(12) United States Patent
Bruckmayer

(10) Patent No.: US 7,632,094 B2
(45) Date of Patent: Dec. 15, 2009

(54) METHOD AND EQUIPMENT FOR PRODUCING GLUCOSE FROM A STARCH SOLUTION

(75) Inventor: Peter Bruckmayer, Velden-Eberspoint (DE)

(73) Assignee: Flottweg GmbH & Co., KGaA (DE)

( * ) Notice: Subject to any disclaimer, the term of this patent is extended or adjusted under 35 U.S.C. 154(b) by 152 days.

(21) Appl. No.: 11/303,213

(22) Filed: Dec. 16, 2005

(65) Prior Publication Data
US 2006/0160190 A1 Jul. 20, 2006

(30) Foreign Application Priority Data
Dec. 17, 2004 (DE) .................... 10 2004 060 929

(51) Int. Cl.
*C12P 19/02* (2006.01)
*C12P 1/00* (2006.01)
*C12P 19/00* (2006.01)
*C12M 1/00* (2006.01)

(52) U.S. Cl. .................... 433/105; 435/41; 435/72; 435/283.1; 435/289.1

(58) Field of Classification Search .................... None
See application file for complete search history.

(56) References Cited
U.S. PATENT DOCUMENTS 2,698,826 A * 1/1955 Peltzer, Sr. .................. 435/161
3,437,267 A * 4/1969 Dahlberg .................... 494/41
4,311,714 A 1/1982 Goering et al.
4,361,651 A 11/1982 Keim
4,398,024 A * 8/1983 Bernert et al. ............... 536/85
4,804,545 A 2/1989 Goering et al.

FOREIGN PATENT DOCUMENTS

| DE | 94 02 088.4 U1 * | 6/1995 |
| DE | 733 646 B1 * | 7/2001 |
| EP | 0 733 646 B1 | 7/2001 |

OTHER PUBLICATIONS

Perrin and Armarego, "Common Physical Techniques in Purification", Purification of Laboratory Chemicals, 4th ed., 1996.*

* cited by examiner

*Primary Examiner*—Christopher R Tate
*Assistant Examiner*—Aaron J Kosar
(74) *Attorney, Agent, or Firm*—Gerald E. Hespos; Anthony J. Casella

(57) ABSTRACT

A method for producing glucose from a starch solution includes a step for saccharification of the starch solution (30) by adding enzymes and/or acid to crude syrup. The method then includes separation of a phase of proteins and/or fats from the crude syrup in a centrifugal separating device (110) and separation of the phase (50) of proteins and/or fats from the centrifugal separating device (110) separately from the residual crude syrup.

7 Claims, 3 Drawing Sheets

METHOD AND EQUIPMENT FOR PRODUCING GLUCOSE FROM A STARCH SOLUTION

BACKGROUND OF THE INVENTION

1. Field of the Invention

The invention relates to a method and to equipment for producing or obtaining glucose from a starch solution.

2. Description of the Related Art

The conversion of starch from a starch solution into glucose or various sugars is an important sector of the starch processing industry and at the same time one of the economically most significant fields of application in food technology. The most important vegetable suppliers of starch for this purpose are maize, potatoes and wheat.

The process of obtaining glucose or dextrose proceeds in various stages. In a first stage a defined starch suspension is generally produced from a previously produced aqueous starch solution and additional water. The starch suspension is liquefied by the addition of water vapour, enzymes and/or acid. A mixture of maltoses (barley sugar) and dextrines (an intermediate form of starch and dextrose) is produced therefrom by means of acid or enzymatic hydrolysis. The starch solution is saccharified by adding additional enzymes and/or acids. During starch saccharification the resultant decomposition products are decomposed further to form simple sugars (monosaccharides). A saccharified crude syrup which is a mixture of glucose (grape sugar) and fructose (fruit sugar) forms. However, the crude syrup also contains important protein and fat contents and substantially unsaccharified constituents which have to be filtered out to produce a finished dextrose product from the saccharified crude syrup.

Filtration is carried out in multi-stage ultrafiltration units or vacuum rotary filters with translucent silica glass (Kieselguhr) as the filtering medium and the undesired by-products, such as fat and protein, are thus separated.

Process steps on an ion exchanger, final cleaning and concentration then follow until finally the desired glucose or dextrose products can be produced in the end state by mixing various qualities of dextrose.

In the above process sequence problems occur in particular during said filtration of the saccharified crude syrup, which problems are reflected in a rapid drop in the power of the filters used, a short service life of these filters, instable process management and high cleaning expenditure and high consumption of filtering auxiliaries.

In the process of obtaining glucose or dextrose it should also be noted that sugar losses are to be avoided as far as possible, and therefore the undesirable by-products, such as fats and protein, have to be removed as far as possible without a simultaneous discharge of sugar. Very high demands are therefore made on the multi-stage ultrafiltration units and vacuum rotary filters used.

SUMMARY OF THE INVENTION

The invention is based on the object of providing a method and equipment for producing glucose from a starch solution which, in contrast to known procedures, can be conducted more economically and, if possible, can simultaneously lead to a higher yield of glucose or dextrose during the course of the process.

This object is achieved according to the invention with a method for producing glucose from a starch solution, comprising the steps: saccharification of the starch solution by adding enzymes and/or acid to saccharified starch solution or crude syrup, separation of a phase substantially comprising proteins and/or fats from the crude syrup in a centrifugal separating device and separation of the phase substantially comprising proteins and/or fats from the centrifugal separating device separately from the residual crude syrup.

Using the method according to the invention the undesired by-products, such as fat and protein, are separated from the saccharified starch solution not by a filtration process but by centrifugal separation. According to the invention the method is therefore not geared to the volume or the dimensions of the particles of the crude syrup to be separated, rather the particles are separated as a function of their specific weight.

This type of separation according to the invention leads to the crude syrup being divided substantially into three phases, namely a phase comprising substantially proteins and/or fats, a phase comprising substantially unsaccharified constituents and a third phase of the residual glucose syrup, which substantially comprises glucose. Of these phases, in particular the phase comprising substantially proteins and/or fats can be efficiently separated from the residual glucose syrup by centrifugal separation, as has been found according to the invention.

It has also been recognised according to the invention that it is precisely the phase comprising substantially proteins and/or fats that is extensively responsible for the fact that problems with respect to a drop in power, the service life, process management and cleaning expenditure repeatedly occur with the filtration units connected downstream. By contrast, problems of this type may be avoided as a result of separation according to the invention and separation of the phase comprising substantially proteins and/or fats from a saccharified starch solution.

Furthermore, sugar losses in the course of the process of obtaining glucose or dextrose can be considerably reduced with the method according to the invention. In tests the sugar losses could be reduced by 50% to 80% compared with known methods. This considerable reduction in losses is based on the fact that, according to the invention, the undesired by-products are purposefully concentrated in a single phase, which by-products can then be removed relatively easily. The residual glucose syrup subsequently has a much higher volume concentration factor, so accordingly considerably more glucose or dextrose can also be obtained from this glucose syrup.

In a method for producing glucose from starch solution the above mentioned unsaccharified constituents of the crude syrup are basically harmless with respect to the further process steps. In an advantageous development of the method according to the invention they are separated nevertheless and separated from the residual glucose syrup then substantially comprising glucose. The total power requirement of subsequent process steps can thus be reduced and the unsaccharified constituents can be returned to the process, optionally in a targeted manner in advance process steps.

Said centrifugal separation processes according to the invention are carried out particularly advantageously in a single centrifugal separating device, in particular in the form of a single decanter. A procedure of this type is particularly favourable with respect to both the required production costs and operating costs. Furthermore, a method of this type leads to particularly low operating and maintenance expenditure.

The saccharified crude syrup treated with the method according to the invention is prepared in such a way that it can be cleaned particularly advantageously in a filtration stage downstream of the centrifugal separating device. As mentioned above, during filtration, according to the invention considerably lower sugar losses occur compared to known methods as the residual glucose syrup to be filtered has a much higher volume concentration factor (what is referred to as VCF).

In addition to the method according to the invention, the object underlying the invention is also achieved with equipment for producing glucose from a starch solution, the equipment being provided with an addition device for adding enzymes and/or acid to the starch solution, a centrifugal separating device for separation of a phase substantially comprising proteins and/or fats from the saccharified crude syrup and also a discharging device for separation of the phase substantially comprising proteins and/or fats from the centrifugal separating device separately from the residual glucose syrup.

This type of equipment according to the invention is advantageously developed so as to correspond to the above-mentioned method in such a way that it is provided with a centrifugal separating device for separation of a phase substantially comprising unsaccharified constituents from the saccharified crude syrup and a discharging device for separation of the phase substantially comprising unsaccharified constituents from the centrifugal separating device separately from the phase substantially comprising proteins and/or fats and separately from the residual glucose syrup then substantially comprising glucose. Alternatively or additionally the equipment can also be configured in such a way that both the phase substantially comprising unsaccharified constituents and the residual glucose syrup are removed from the centrifugal separating device in a single volume stream by the discharging device.

By integrating said centrifugal separating processes according to the invention in a single centrifugal separating device, in particular in the form of a decanter, a particularly inexpensive solution that is especially easy to incorporate in terms of process engineering is created.

The equipment according to the invention is also advantageously developed in that the centrifugal separating device, and in particular the decanter, is provided with a paring disc device or impeller for discharging the residual glucose syrup substantially comprising glucose. A device of this type comprising a paring disc is particularly good for removing the residual glucose syrup as it can be very variably adjusted. This is particularly important in this regard as the quality and composition of the crude syrup to be industrially processed can be very different. Despite the various syrup qualities and types, in an advantageous development of the invention a paring disc device is provided, of which the paring disc diameter is purposefully adjustable in such a way that it has a ratio to the internal diameter of the drum of between approximately 0.64 and approximately 0.76, particularly advantageously between approximately 0.70 and approximately 0.72. Despite different throughputs and syrup qualities a high-quality residual glucose syrup that has been removed can be attained with a paring disc diameter of this type.

The removal according to the invention of the residual glucose syrup can also be advantageously influenced in that the centrifugal separating device, and in particular the decanter, is provided with a counterpressure device for generating a banking-up pressure at a discharge of the residual glucose syrup substantially comprising glucose. With this type of generation of counterpressure at the discharge of the residual glucose syrup the flow of the latter is affected within the centrifugal separating device in such a way that a particularly advantageous discharge of the phase substantially comprising proteins and/or fats results. In the method according to the invention for producing glucose the phase substantially comprising proteins and/or fats forms, in particular, a floating component on the residual glucose syrup substantially comprising glucose, which floating component can advantageously be conveyed by a correspondingly affected flow of the glucose syrup in the centrifugal separating device to the discharging device, which is provided for separating the phase substantially comprising proteins and/or fats. To achieve a discharge of the floating component that is as stable as possible during operation of the equipment according to the invention, it has been ascertained according to the invention that the counterpressure of the residual glucose syrup should be between approximately 0.5 bar and approximately 3 bar.

The centrifugal separating device according to the invention is also advantageously provided at the discharging device for separating the phase substantially comprising proteins and/or fats with a conveying aid. The discharge of separated fat and protein as undesirable by-products can be purposefully separated for a subsequent filtration process by means of the conveying aid. The conveying aid can advantageously be configured as a screw or screw helix with which what is known as "helical discharge" is possible. As already described above, in the centrifugal separating device according to the invention the phase substantially comprising proteins and/or fats is a floating component which floats on the residual glucose syrup substantially comprising glucose. A floating component of this type is conventionally removed in known centrifugal separating devices by means of an overflow weir. By contrast, according to the invention a helical discharge, as has previously only been provided in centrifugal separating devices, which is provided for separating a mixture into a solid phase, a liquid phase and a second solid phase, is provided for removing the phase substantially comprising proteins and/or fats. In other words, in said development according to the invention a solid-liquid-solid centrifugal machine is used for separating a solid-liquid-liquid mixture. The centrifugal separating device according to the invention is in the process advantageously provided with a second screw helix for removing the phase substantially comprising unsaccharified constituents (which according to the conventional definition is a solid phase), which second screw helix is arranged on the discharging device for separating the phase substantially comprising unsaccharified constituents.

To further improve separation of the phase substantially comprising proteins and/or fats a conveying cone is also advantageously provided on the associated discharging device, the angle of slope of which cone is configured in a range between approximately 10° and approximately 20°, in particular between approximately 15° and approximately 17°. A conveying cone inclined in this way leads to particularly good separation results, even in the case of very different qualities of starch solution. It has been determined according to the invention that in the case of conveying cone angles of slope which are flatter with respect to the longitudinal axis of the decanter, the separation zone of the floating component is disadvantageously reduced. On the other hand, the conveying capacity on the conveying cone deteriorates with larger angles of slope.

Alternatively or additionally the quality of the centrifugal separation according to the invention of starch solution can be further improved before a subsequent filtration process in that said conveying cone is purposefully configured with an uneven surface. A surface of this type can, for example, be roughened or provided with conveying strips, and is used in this form as an adhering surface for the phase rising on the conveying cone or the floating component comprising fat and protein. The conveying capacity of this floating component is consequently increased and a higher quality separation result is achieved overall.

Separation of the floating component from the centrifugal separating device according to the invention can also be advantageously influenced in that the centrifugal separating device, and in particular the decanter at the discharging device for separating the phase substantially comprising unsaccharified constituents, is provided with a banking-up device for increasing the conveying pressure of the phase substantially comprising proteins and/or fats from the associated discharging device. The banking-up device is advantageously configured as a diaphragm plate or a baffle plate which, starting from a screw body, extends radially outwardly substantially transversely to or along the screw axis and forms a barrier which prevents floating components from floating on the residual glucose syrup substantially comprising glucose, in the direction of the discharge of the phase substantially comprising unsaccharified constituents. The diaphragm plate or the baffle plate is particularly advantageously configured to be of such a size in diameter that it comes close to the diameter of a screw helix of said screw body. The floating component that has banked up on the diaphragm plate or baffle plate in this way generates a conveying pressure in the direction of the discharging device of the floating component.

So that the banked-up floating component or the phase substantially comprising proteins and/or fats can float as freely as possible on the residual glucose syrup of the associated discharge, in a further advantageous configuration of the equipment according to the invention the centrifugal separating device is configured with a screw helix, of which the screw body substantially does not comprise an opening between an inlet for the starch solution and the discharging device for separating the phase substantially comprising proteins and/or fats. Said screw body is accordingly configured in said portion with a smooth surface which does not have any potential banked-up regions for floating components on the screw body.

The screw helix/helices already described above, and which can be provided as conveying aids for discharging the phase substantially comprising proteins and/or fats and optionally the phase substantially comprising unsaccharified constituents in the centrifugal separating device according to the invention, is/are operated particularly advantageously during operation in the associated drum in a lagging mode of operation. "Lagging" in this connection is taken to mean that the screw helix rotates more slowly than the drum. The lagging mode of operation assists the discharge of floating component from the centrifugal separating device according to the invention as the residual glucose syrup substantially comprising glucose travels in the direction of the discharging device which is used for separating the phase substantially comprising proteins and/or fats.

The centrifugal separating device according to the invention is also particularly advantageously configured with a drum which is configured with a diameter to length ratio of between 1 to 3 and 1 to 5, in particular approximately 1 to approximately 4. This type of dimensioning of the drum contributes to the construction of a stable floating component section during operation of the device. The clear result attained is accordingly of a high quality.

The last mentioned details and advantages achieved therewith of the separating device according to the invention are particularly significant if a filtration device follows centrifugal separation in the process chain, in which device the residual glucose syrup substantially comprising glucose can be cleaned further.

The object according to the invention is finally also achieved with a decanter for separating a three-phase mixture in a centrifugal separation procedure, which comprises a first discharging device for separating a sedimenting phase from the mixture and a second discharging device for separating a floating phase from the mixture.

The two discharging devices are each configured with a screw helix and an associated discharging cone and the discharging device which is used for separating the sedimenting phase is provided according to the invention with a diaphragm plate or a baffle plate for banking-up the floating phase before the discharge opening of the sedimenting phase. With a decanter of this type and the diaphragm plate or baffle plate arranged therein according to the invention, as described above, a solid-liquid-liquid phase mixture with an at least viscous floating phase can also be processed with the centrifugal separating device actually operating as a solid-liquid-solid machine.

So that separation of the requisite quality of a solid-liquid-liquid mixture can be achieved with said machine the diaphragm plate or baffle plate provided according to the invention is particularly advantageously configured with a diameter of approximately 0.75 to approximately 0.95 of the internal diameter of an associated drum of the decanter.

Moreover the object is achieved according to the invention by using a decanter which is provided with a sediment separation stage and a floating component separation stage in order to thus obtain glucose from a starch solution. The floating component separation stage of the decanter is used according to the invention for separation of a phase substantially comprising proteins and/or fats from the starch solution and the sediment separation stage of the decanter is used for separating a phase substantially comprising unsaccharified constituents from the starch solution. Residual glucose syrup substantially comprising glucose can thus be obtained from the starch solution and can be processed particularly efficiently in a subsequent filtration process and also has a particularly high sugar concentration.

An embodiment of a method according to the invention for producing or obtaining glucose from a starch solution will be described in more detail hereinafter with the aid of the accompanying schematic drawings, in which:

DETAILED DESCRIPTION OF THE PREFERRED EMBODIMENTS

Figure 1:
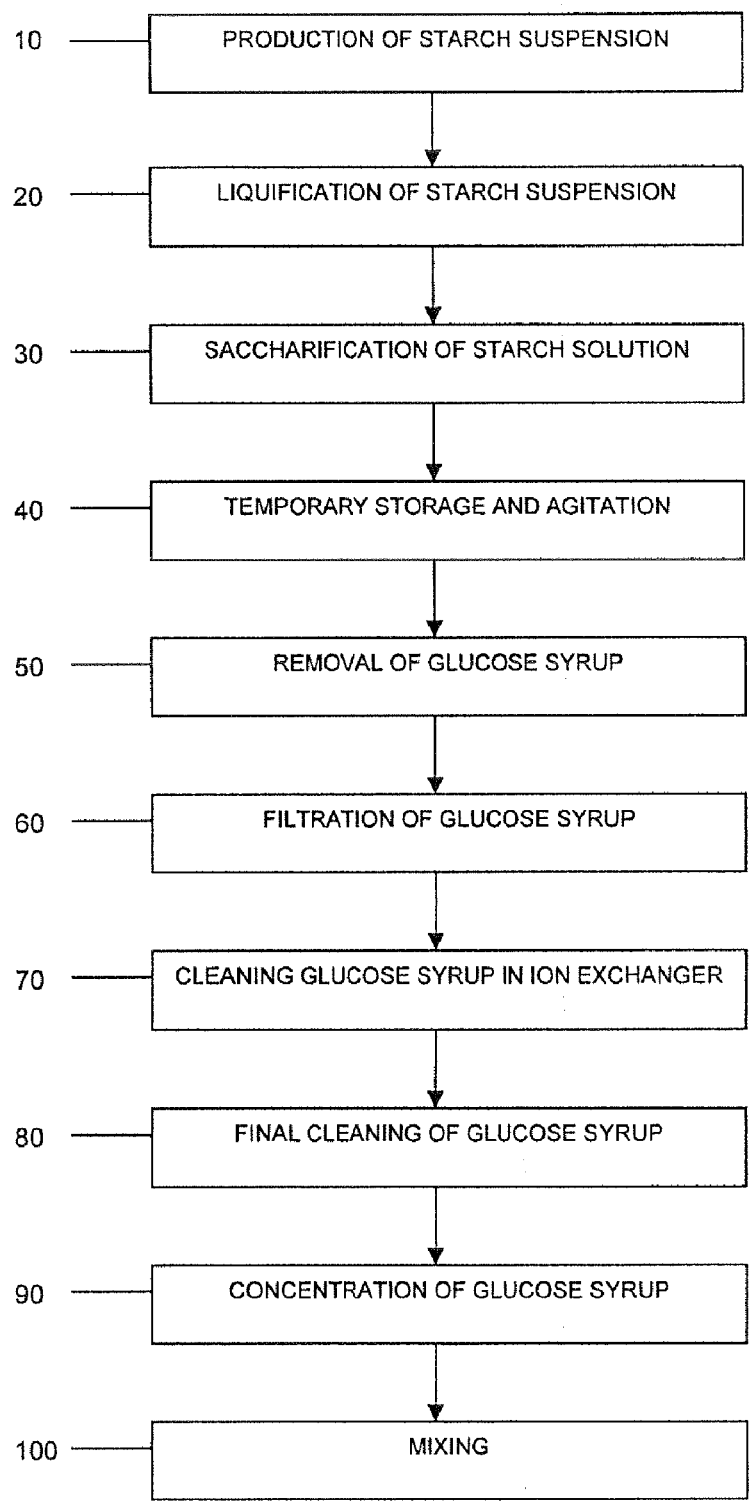
FIG. 1 shows a flowchart of a method according to the invention for producing glucose from a starch solution.

The method illustrated in FIG. 1 is used for producing glucose from a starch solution which, for example, has been obtained from maize, potatoes or wheat. The starch solution is firstly produced in a process step 10 as a starch suspension from starch milk and water. The starch suspension is subsequently liquefied in a process step 20 by adding water vapour, enzymes and/or acid. By adding further enzymes and acid, saccharification of the starch solution is subsequently stimulated in a process step 30.

In a process step 40 the starch solution saccharified in this way is temporarily stored as a crude syrup in a storage tank and agitated with an agitator in such a way that a comparatively homogeneous mixture of crude syrup, which comprises insoluble proteins and fats, glucose or dextrose as well as unsaccharified constituents, can be removed from the storage tank.

The crude syrup removed is subjected to centrifugal separation in a process step 50 and in the process a phase substantially comprising proteins and/or fats is separated and a phase substantially comprising unsaccharified constituents is separated separately therefrom. A glucose syrup which substantially comprises glucose is separated using centrifugal separation of this type. This glucose syrup is subjected in a process step 60 to filtration in an ultrafiltration device. Cleaning in an ion exchanger follows according to the illustrated process step 70 and lastly final cleaning follows according to a process step 80. The glucose syrup cleaned in this manner is concentrated in a process step 90 and finally a finished glucose end product is produced by mixing various qualities of glucose or dextrose in a process step 100.

Figure 2:
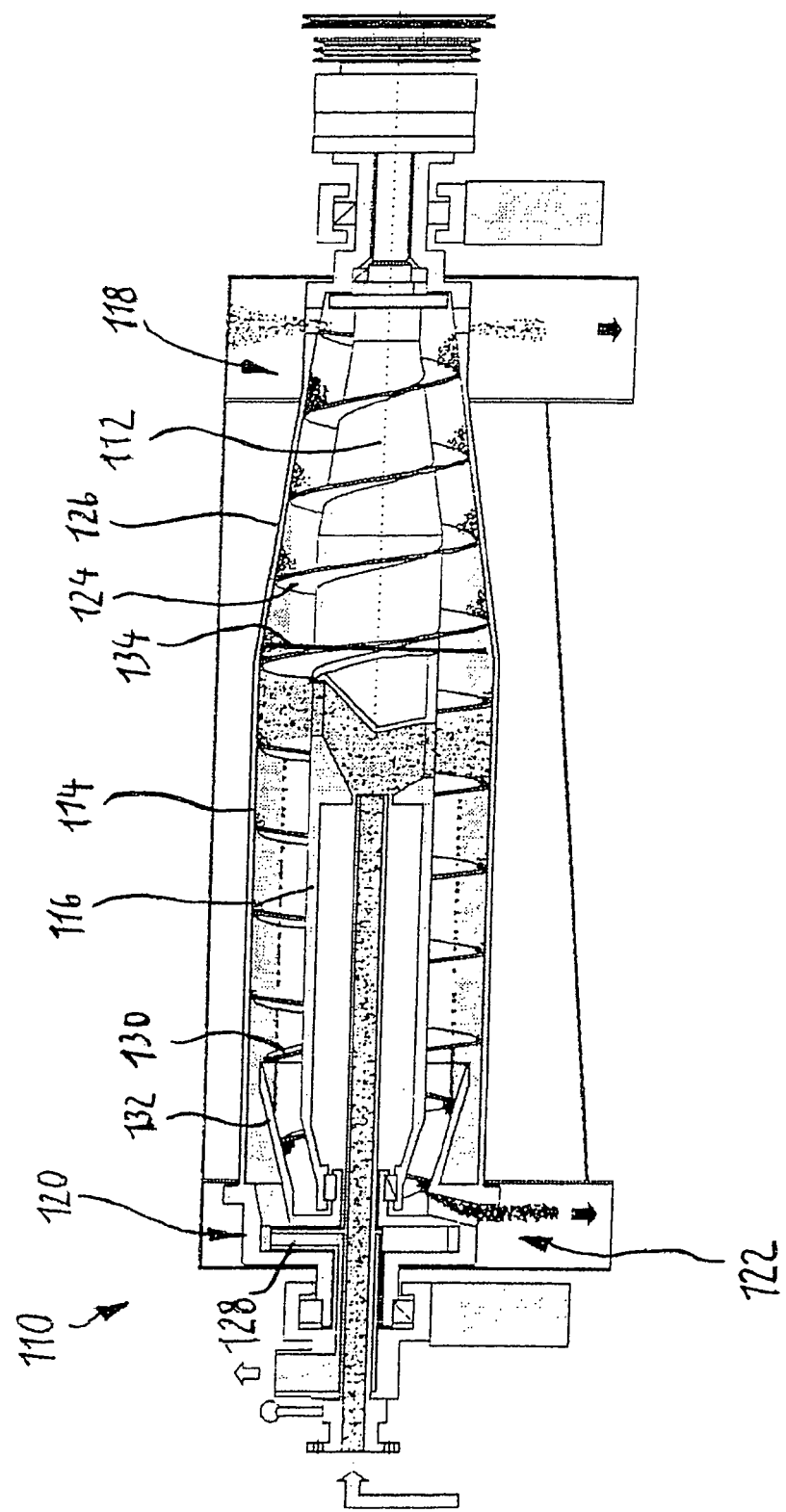
FIG. 2 shows a longitudinal section of a first embodiment of a centrifugal separating device which is used in the method according to FIG. 1.

FIG. 2 shows in longitudinal section a centrifugal separating device 110 as is used for the above-mentioned process step 50 of centrifugal separation. The centrifugal separating device 110 is configured with a horizontal axis 112 of rotation around which a drum 114 rotates at a high speed during operation of the centrifugal separating device 110. A screw body 116, which can also be set into rotation, extends along the axis 112 of rotation in the drum 114.

A total of three devices for discharging a respective phase from the saccharified starch solution fed into the drum 114 are located on the drum 114.

Thus a discharging device 118 for a phase substantially comprising unsaccharified constituents and a discharge 120 for a residual glucose syrup substantially comprising glucose are provided. A discharging device 122 is also arranged on the drum 114 and is provided for discharging a phase substantially comprising proteins and/or fats.

The discharging device 118 for the phase substantially comprising unsaccharified constituents is configured with a first screw helix 124 which can convey sediment accumulating on the inner side of the drum 114 along a first discharging cone 126 radially inwardly out of the crude syrup located in the drum 114. The first discharging cone 126 in the process forms an end portion of the drum 114, arranged on the right, based on FIG. 2.

The discharge 120 for the residual glucose syrup substantially comprising glucose is configured with a paring disc device 128 which is located at the opposing end of the drum 114 in the first discharging cone 126. The paring disc device 128 is configured with a paring disc diameter which has a ratio to the internal diameter of the drum of approximately 0.71.

The discharging device 122 for the phase substantially comprising proteins and/or fats is configured with a second screw helix 130 which is located on the end region of the screw body 116 directed toward the paring disc device 128 (based on FIG. 2, in other words at the left-hand end portion of the screw body 116). The diameter of the second screw helix 130 is configured overall so as to be smaller than that of the first screw helix 124 and is partially surrounded by a second discharging cone 132 which submerges with an end region into the saccharified starch solution situated in the drum 114 and subject to centrifugal force.

Owing to its comparatively low specific weight the phase substantially comprising proteins and/or fats is moved radially inwardly from the starch solution by said centrifugal effect and forms a floating component at this location, which component floats on the residual glucose syrup substantially comprising glucose. This floating component is conveyed out of the centrifugal separating device 110 along the second discharging cone 132 with the aid of the second screw helix 130. In the process the floating component thus adheres better to the second discharging cone 132 if the second discharging cone 132 is configured with a roughened surface.

The discharge of floating component or the phase substantially comprising proteins and/or fats is further improved in that a diaphragm plate 134 is formed within the first screw helix 124. The diaphragm plate 134 is arranged in the region of the first screw helix 124 where it passes from the substantially cylindrical portion of the drum 114 into the portion of the first discharging cone 126. The diaphragm plate 134 is formed in this case as a circular disc extending transversely to the axis 112 of rotation. It is configured with a diameter which corresponds to approximately 0.9 of the internal diameter of the associated drum 114 in the region of the arrangement of the diaphragm plate 134.

Figure 3:
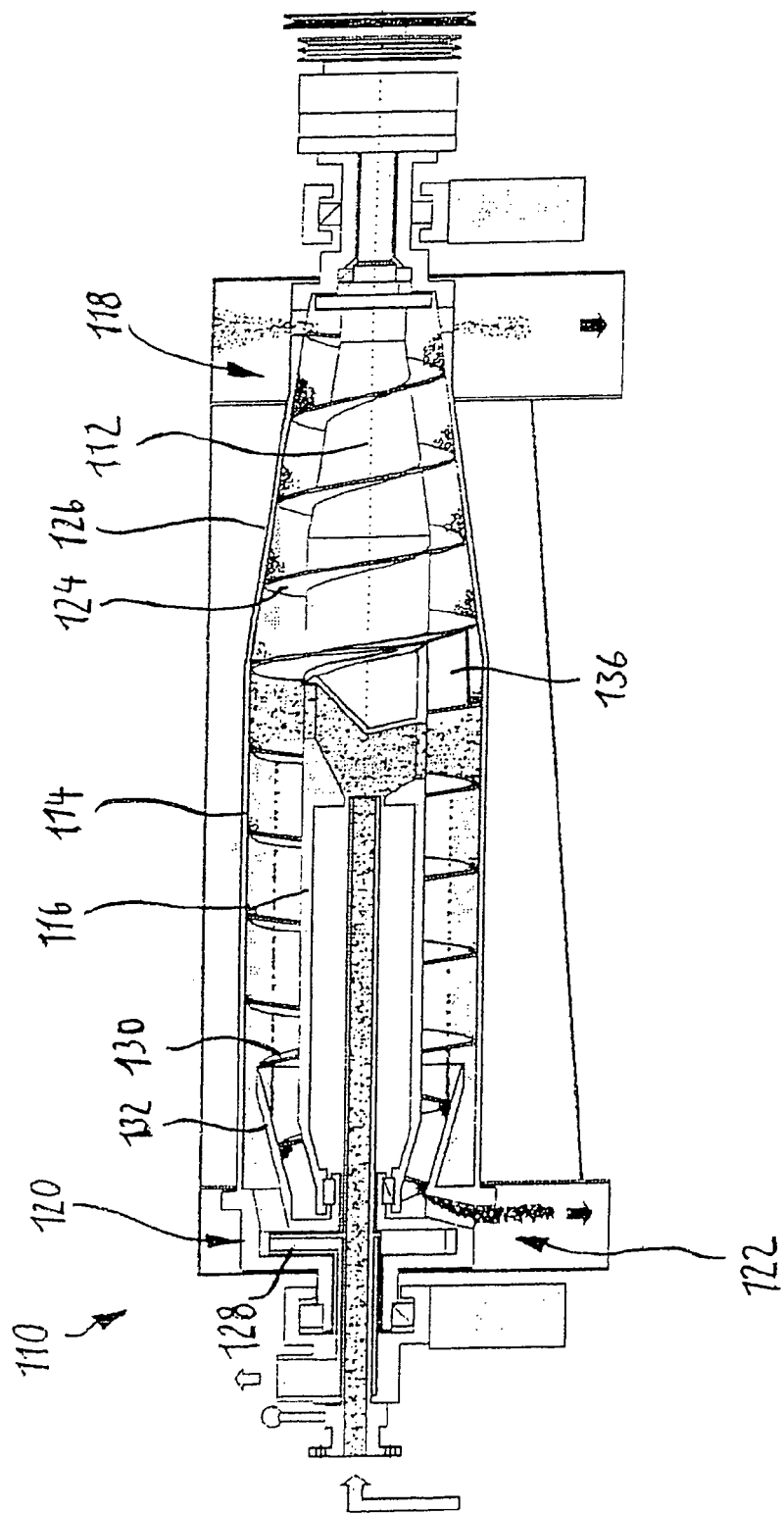
FIG. 3 shows a longitudinal section of a second embodiment of a centrifugal separating device which is used in the method according to FIG. 1.

FIG. 3 shows an embodiment of a centrifugal separating device according to the invention which substantially corresponds to that in FIG. 2. The same discharge 120 for residual glucose syrup substantially comprising glucose and the same discharging device 122 for a phase substantially comprising proteins and/or fats are provided in particular in the centrifugal separating device of FIG. 3. In the centrifugal separating device 110 according to FIG. 3 by contrast, a baffle plate 136 is provided instead of a diaphragm plate with respect to the discharging device 118 for a phase substantially comprising unsaccharified constituents.

The baffle plate 136 is configured as a weir which is located between two pitches of the first screw helix 124 and, more precisely, in the portion of the screw helix 124 at which the substantially cylindrical portion of the drum 114 also passes into the portion of the first discharging cone 126. The baffle plate 136 extends radially outwardly substantially parallel to the axis 112 of rotation and in the process projects into the drum 114 to about 0.85 of the internal diameter thereof.

What is claimed is:

1. A method of producing a residual glucose syrup from a starch solution, the method comprising:
    (a) saccharifying a starch solution by adding enzymes and/or acid to said starch solution thereby producing a crude syrup;
    (b) centrifuging the crude syrup in a centrifugal separating device (110), wherein the device is configured with a horizontal axis of rotation, a drum, and a screw body therein, said centrifuging of said crude syrup comprising separating a residual glucose syrup substantially comprising glucose (a') from a phase substantially comprising proteins and/or fats (b'), wherein said phase has a lower specific weight than the specific weight of said residual glucose syrup and wherein said separating provides forming said phase (b') floating on said residual glucose syrup (a');
    (c) conveying the phase (b') to a discharge device along the screw body of the centrifugal separating device, thereby retaining the residual glucose syrup substantially comprising glucose (a'); and then,
    (d) obtaining said residual glucose syrup (a') from said centrifugal separating device.

2. The method of claim 1, wherein said separating (i) further comprises separating a phase substantially comprising unsaccharified constituents (c') from the phase (b') and the residual glucose syrup (a').

3. The method of claim 2, wherein the centrifugal separating device is a single centrifugal separating device in the form of a single decanter.

4. The method of claim 1, further comprising cleaning the residual glucose syrup (a'), said cleaning comprising filtering said syrup (a') in a filtration stage (60) downstream from the centrifugal separating device.

5. A method for producing a residual glucose syrup from a starch solution, the method comprising:
  (a) saccharifying the starch solution by adding enzymes and/or acid to the starch solution thereby producing a crude syrup;
  (b) centrifuging the crude syrup in a centrifugal separating device (110), wherein the device is configured with a horizontal axis of rotation, a drum and a screw body therein, said centrifuging of said crude syrup comprising separating a residual glucose syrup substantially comprising glucose (a') from a phase substantially comprising proteins and/or fats (b'); and
  (c) conveying the phase (b') to a discharge device my means of a screw helix of the centrifugal separating device to retain the residual glucose syrup (a'); and then,
  (d) obtaining said residual glucose syrup (a') from said centrifugal separating device.

6. A method of producing a residual glucose syrup from a starch solution, the method comprising:
  (a) saccharifying the starch solution by adding enzymes and/or acid to the starch solution thereby producing a crude syrup;
  (b) centrifuging the crude syrup in a centrifugal separating device (110), wherein the device is configured with a horizontal axis of rotation and a screw helix therein, said centrifuging of said crude syrup comprising separating a residual glucose syrup substantially comprising glucose (a') from a phase comprising proteins and/or fats (b'); and
  (c) conveying the phase (b') to a discharge device my means of the screw helix of the centrifugal separating device while retaining the residual glucose syrup (a'); and then, obtaining said residual glucose syrup (a') from said centrifugal separating device.

7. A method of producing a residual glucose syrup from a starch solution, the method comprising:
  (a) saccharifying the starch solution by adding enzymes and/or acid to the starch solution thereby producing a crude syrup;
  (b) centrifuging the crude syrup in a centrifugal separating device (110), wherein the device is configured with a horizontal axis of rotation, a first screw helix, and a second screw helix therein, said centrifuging of said crude syrup comprising forming a first substantially liquid phase comprising a residual glucose syrup that comprises glucose (a') from a second substantially liquid phase substantially comprising proteins and/or fats (b'), wherein said second substantially liquid phase (b') has a lower specific weight than the specific weight of said first phase (a') and of a third substantially solid phase comprising unsaccharified constituents (c'), wherein said separating provides forming said phase (b') floating on said residual glucose syrup (a');
  (c) conveying the phase (b') to a discharge device along the screw body of the centrifugal separating device, thereby retaining the residual glucose syrup comprising glucose (a');
  (d) discharging the substantially liquid second phase (b') floating on the substantially liquid first phase (a') from the centrifugal separating device, comprising conveying the substantially liquid second phase (b') to a first discharge device by means of the first screw helix;
  (e) discharging the substantially solid third phase comprising unsaccharified constituents (c') from the centrifugal separating device, comprising conveying the substantially solid third phase to a second discharge device by means of the second screw helix; and then
  (f) obtaining said residual glucose syrup (a') from said centrifugal separating device.

\* \* \* \* \*